United States Patent [19]
Javitt

[11] Patent Number: 5,837,730
[45] Date of Patent: Nov. 17, 1998

[54] TREATMENT OF NEGATIVE AND COGNITIVE SYMPTOMS OF SCHIZOPHRENIA WITH GLYCINE UPTAKE ANTAGONISTS

[76] Inventor: Daniel C. Javitt, 3043 Johnson Ave., Riverdale, N.Y. 10463

[21] Appl. No.: 759,681

[22] Filed: Dec. 6, 1996

Related U.S. Application Data

[60] Provisional application No. 60/008,361 Dec. 7, 1995.

[51] Int. Cl.$^6$ .......................... A61K 31/22; A61K 31/195
[52] U.S. Cl. ........................... 514/551; 514/561; 514/563
[58] Field of Search .................................. 514/561, 551, 514/563

[56] References Cited

U.S. PATENT DOCUMENTS

| | | |
|---|---|---|
| 4,904,681 | 2/1990 | Cordi et al. . |
| 5,068,412 | 11/1991 | Ohfune et al. . |
| 5,086,072 | 2/1992 | Trullas et al. . |
| 5,179,085 | 1/1993 | Bigge et al. . |
| 5,187,171 | 2/1993 | Cordi et al. . |
| 5,260,324 | 11/1993 | Cordi et al. . |
| 5,428,069 | 6/1995 | Skolnick et al. . |

OTHER PUBLICATIONS

Andreasen N (1989): The scale for the assessment of negative symptoms (SANS): conceptual and theoretical foundations. Br J Psychiatry 155 (suppl. 7):49–52.
Costa J, Khaled E, Sramek J, Bunney W Jr, Potkin SG (1990): An open trial of glycine as an adjunct to neuroleptics in chronic treatment–refractory schizophrenics. J Clin Psychopharmacol 10:71–72.
D'Souza DC, Morrissey K, Abi–Saab D, Damon D, Gil R, Bennett A, Krystal JH (1995): Intravenous glycine and oral D–cycloserine effects on CSF amino acids, plasma hormones, and behavior in healthy humans: Implications for schizophrenia. Schiz Res 15:147, 1995.
Javitt DC and Zukin SR (1991): Recent advances in the phencyclidine model of schizophrenia. Am J Psychiatry 148: 1301–1308.
Javitt DC, Zylberman I, Zukin SR, Heresco–Levy U, Lindenmayer JP (1994): Amerlioration of negative symptoms in schizophrenia by glycine. Am J Psyciatry 151:1234–1236.
Johnson JW. Ascher P. Glycine potentiates the NMDA response in cultured mouse brain neurons. Nature. 325:529–31, 1987.
Kay SR, Fizbein A, Opler LA (1987): The positive and negative syndrome scale (PANSS) for schizophrenia. Schiz Bull 13:261–276.
Leiderman Eduardo, Zylberman Ilana, Zukin Stephen R., Cooper Thomas B, Javitt Daniel C. (1986): Preliminary Investigation of High–Dose Oral Glycine on Serum Levels and Negative Symptoms in Schizophrenia: An Open–Label Trial. Biol Psychiatry 39:213–215.
Potkin SG, Costa J, Roy S, Sramek J, Jin Y, Gulasekaram B (1992): Glycine in the treatment of schizophrenia —theory and preliminary results, in Novel Antipsychotic Drugs. Edited by Meltzer HY. New York, Raven Press.

Rosse RB, Theut SK, Banay–Schwartz M, Leighton M, Scarcella E, Cohen CG, Deutsch SI (1989): Glycine adjuvant therapy to conventional neuroleptic treatment in schizophrenia: an open–label, pilot study. Clin Neuropharmacol 12:416–24.

Waziri R (1989): Glycine therapy of schizophrenia. Biol Psychiatry 1988, 23:210–211 [letter].

Toth Eugene, Weiss Benjamine, Banay–Schwartz Miriam, Lajtha Abel (1986): Effect of Glycine Derivatives on Behavioral Changes induced by 3–Mercaptopropionic Acid or Phencyclidine in Mice. 11:1–8.

Guastella J, Brecha N, Weigmann C, Lester HA, Davidson N (1992) Cloning, expression, and localization of a rat brain high–affinity glycine transporter. Proc Natl Acad Sci USA 89:7189–7193.

Jackson DM, Johansson C, Lindgren L–M, Bengtsson A (1994) Dopamine receptor antagonists block amphetamine– and phencyclidine–induced motor stimulation in rats. Pharmacol Biochem Behav 48:465–471.

Liu Q–R, Lopez–Corcuera B, Mandiyan S, Nelson H, Nelson, N (1993) Cloning and expression of a spinal cord–and brain–specific glycine transporter with novel structural features. J Biol Chem 1993; 268:22802–22808.

Smith KE, Borden LA, Hartig PR, Branchek T, Weinshank RL (1992) Cloning and expression of a glycine transporter reveal colocalization with NMDA receptors. Neuron 8: 927–935.

Tanii Y, Nishikawa T, Hashimoto A, Takahashi K (1994) Stereoselective antagonism by enantiomers of alanine and serine of phencyclidine–induced hyperactivity, stereotypy and ataxia in the rat. J Pharmacol Exp Ther 269: 1040–1048.

Toth E, Lajtha A (1986) Antagonism of phencyclidine–induced hyperactivity by glycine in mice. Neurochem Res 11: 393–400.

Zafra F, Aragon C, Olivares L, Danbolt NC, Gimenez C, Storm–Mathisen J (1995) Glycine transporters are differentially expresses among CNS cells. J Neurosci 15:3952–3969.

*Primary Examiner*—William R. A. Jarvis
*Attorney, Agent, or Firm*—Sughrue,Mion,Zinn,Macpeak & Seas, PLLC

[57] ABSTRACT

A glycine uptake antagonist is administered for augmenting NMDA receptor-mediated neurotransmission treating symptoms of psychosis and of schizophrenia.

12 Claims, 16 Drawing Sheets

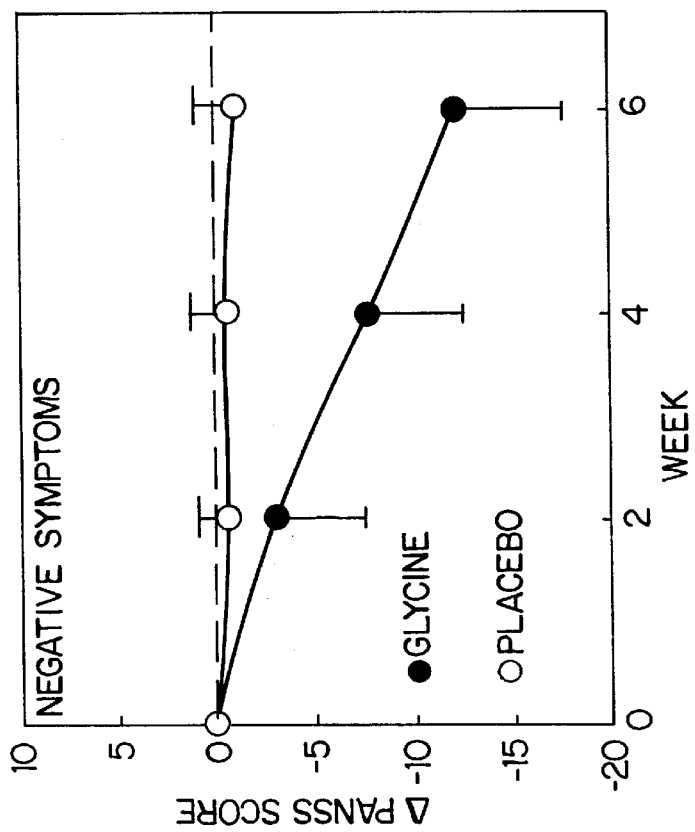
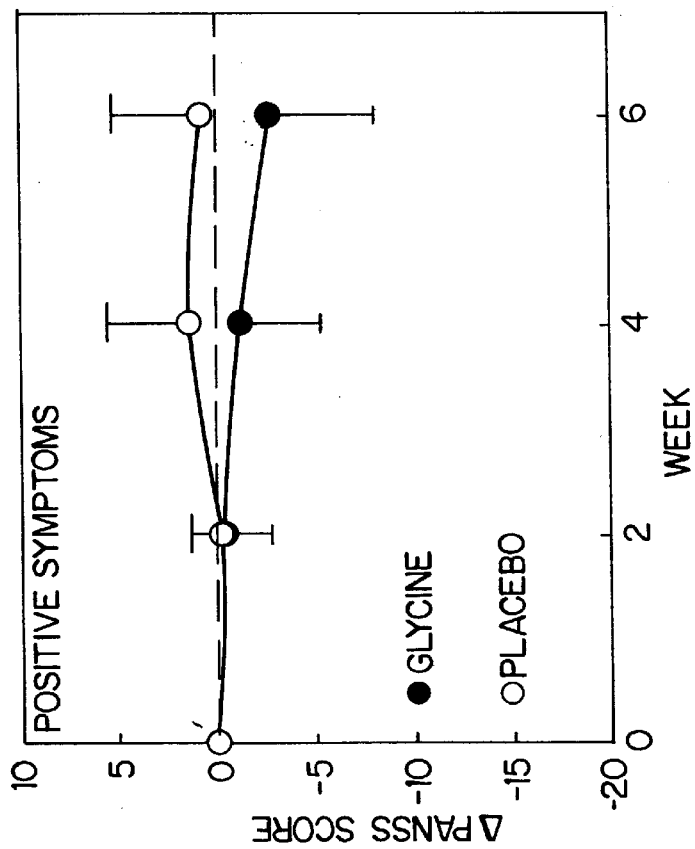

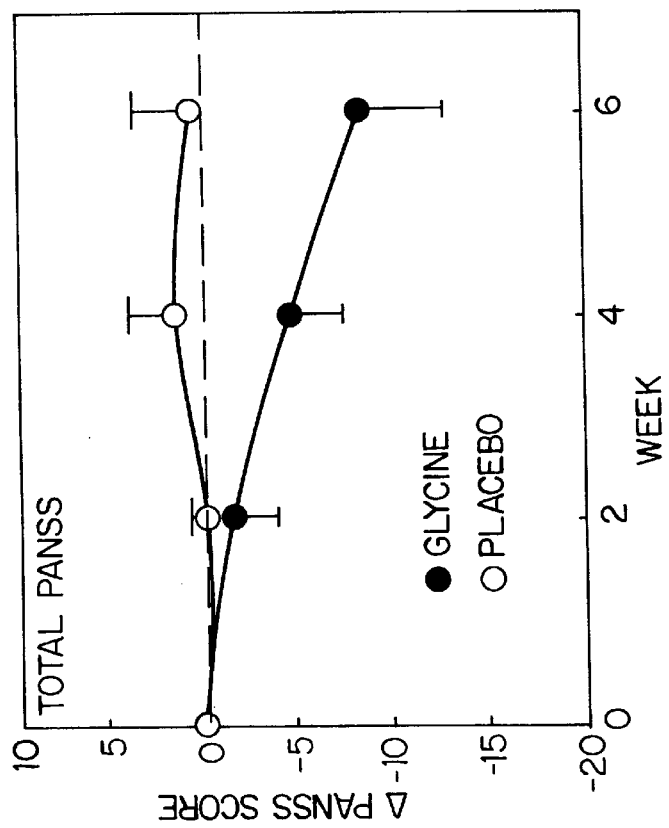
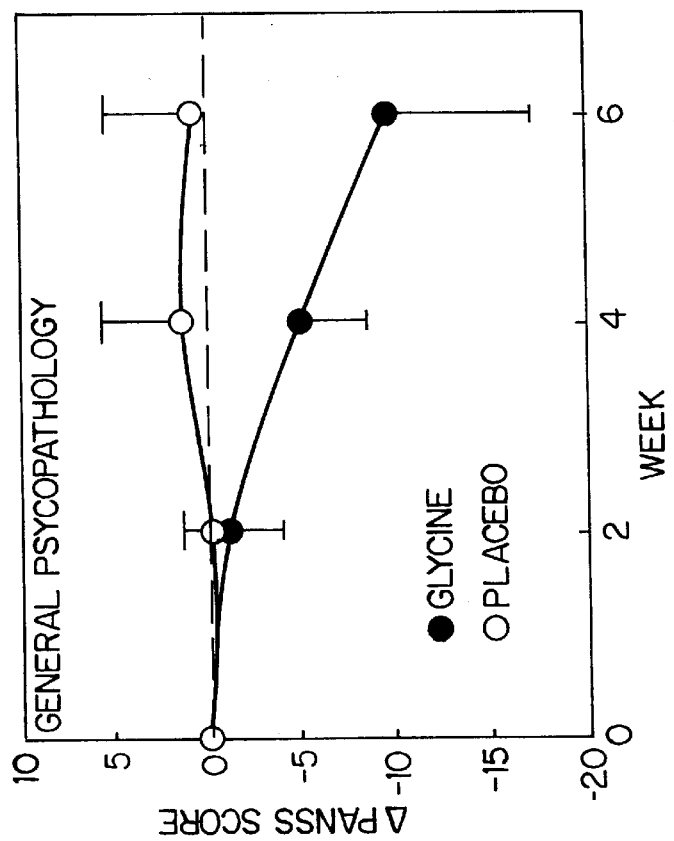
FIG. 2(c)
FIG. 2(d)

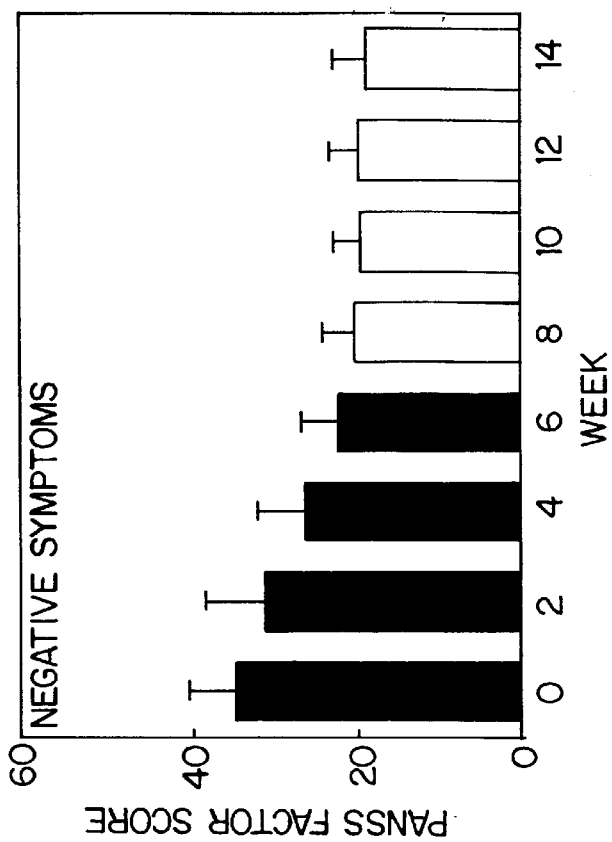
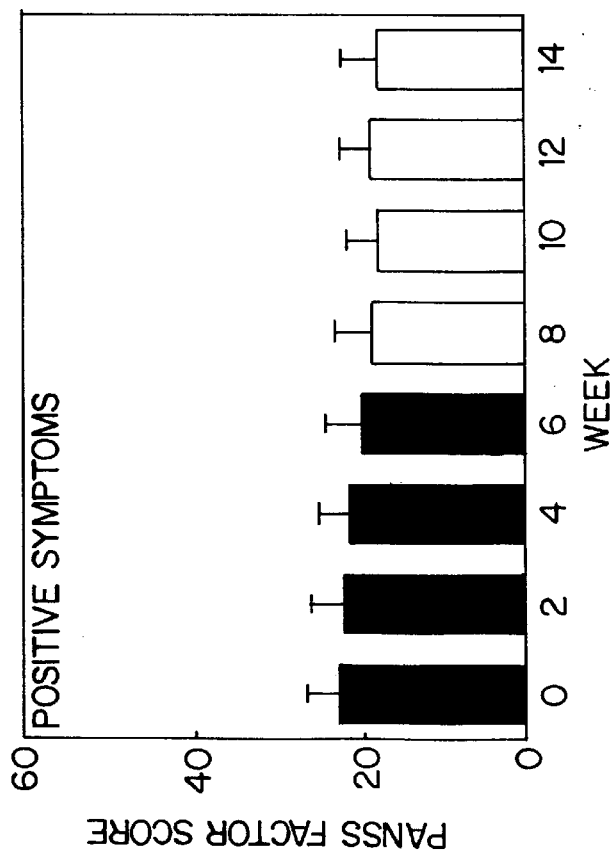
FIG. 3(a)
FIG. 3(b)

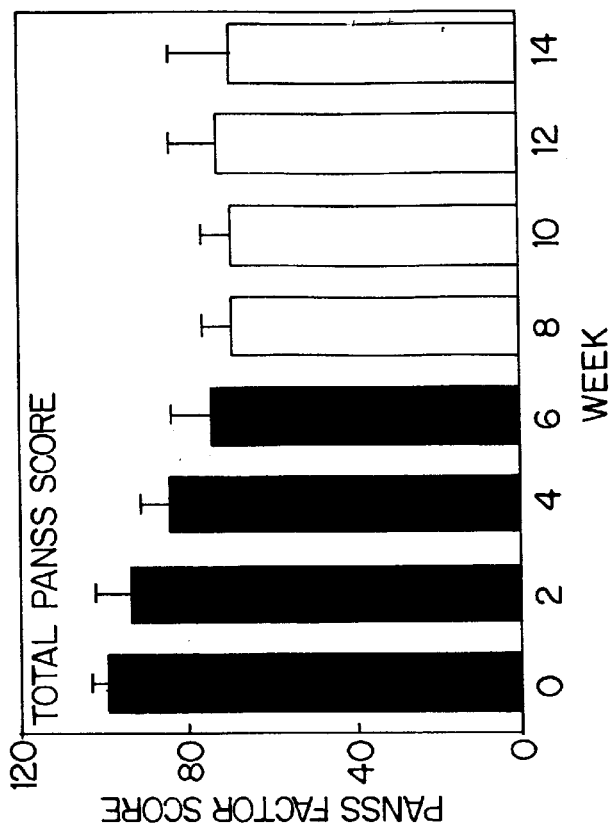
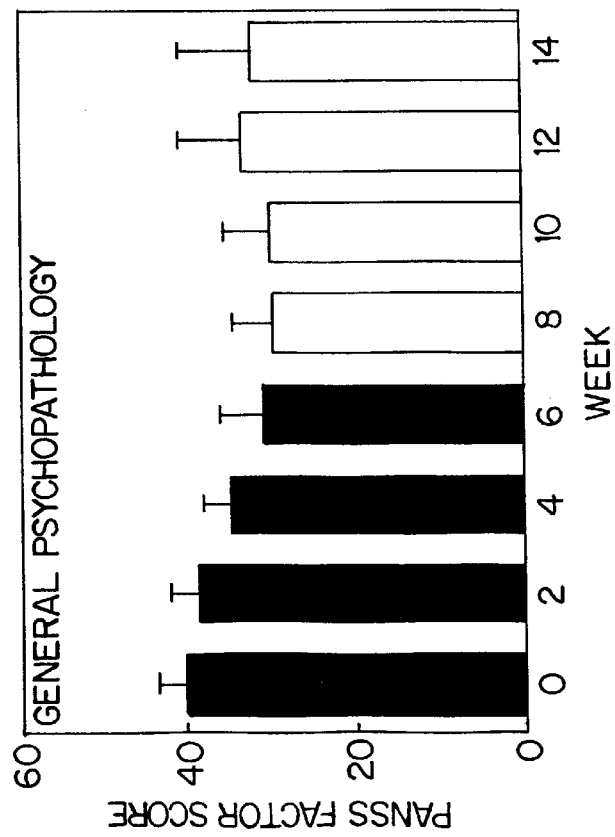

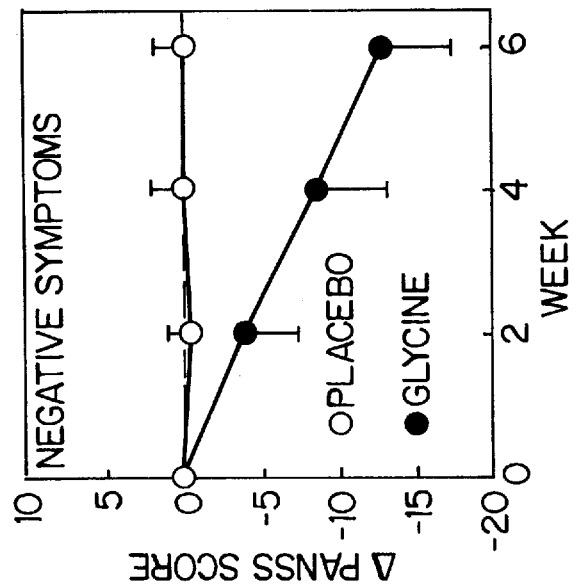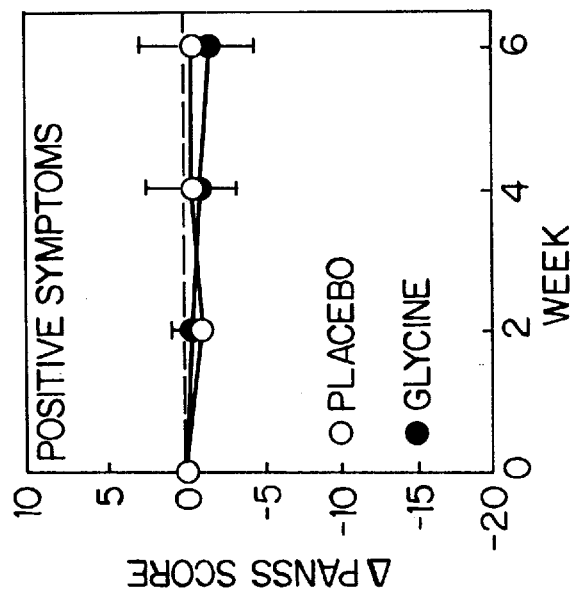

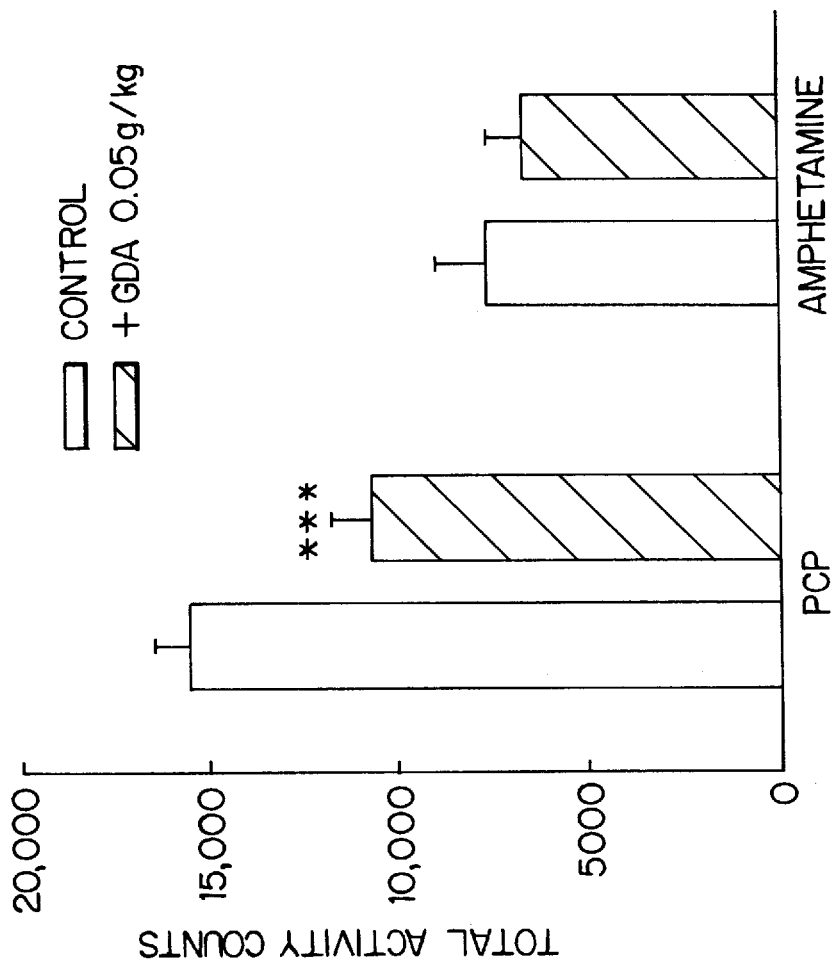

TREATMENT OF NEGATIVE AND COGNITIVE SYMPTOMS OF SCHIZOPHRENIA WITH GLYCINE UPTAKE ANTAGONISTS

RELATED APPLICATION

This application claims benefit of provisional application 60/008,361 filed Dec. 7, 1995.

BACKGROUND OF THE INVENTION

For the past 30 years, the dopamine hypothesis has been the leading neurochemical model of schizophrenia. The dopamine hypothesis is based upon observations that amphetamine-like dopamine releasing agents induce a psychotomimetic state that closely resembles schizophrenia and that agents that block dopamine receptors (e.g., chlorpromazine, haloperidol) are clinically beneficial in the treatment of schizophrenia. The dopamine hypothesis posits that symptoms of schizophrenia reflect functional hyperactivity of brain dopaminergic symptoms, primarily in the mesolimbic and mesocortical brain regions. Despite its heuristic value, however, there are several limitations of the dopamine hypothesis that have contributed to limitations in clinical treatment in schizophrenia. First, amphetamine psychosis provides an accurate model only for the positive symptoms of schizophrenia (e.g., hyperactivity, hallucinations). In contrast, amphetamine administration does not lead to the development of negative symptoms (e.g., blunted affect, emotional withdrawal) or cognitive dysfunction similar to that observed in schizophrenia. A significant percentage (20–50%) of schizophrenic patients continue to show prominent negative symptoms and thought disorder despite optimal treatment with dopamine-blocking agents, indicating that new treatment approaches are necessary. Second, for the majority of schizophrenic patients no clear disturbances of dopaminergic neurotransmission have been demonstrated. Thus, to the extent that functional dopaminergic hyperactivity does exist, it may be secondary to a more fundamental disturbance in other neurotransmitter systems. Antidopaminergic treatment, therefore, while controlling symptoms may not address underlying pathophysiology.

A potential direction for the development of a new treatment approach first became available in the late 1950's with the development of phencyclidine (PCP, "angel dust"). PCP was initially developed for use as a general anesthetic. In early clinical trials, PCP and related agents (e.g., ketamine) were found to induce psychotic symptoms that closely resembled those of schizophrenia. As opposed to amphetamine psychosis, PCP psychosis incorporated both negative and positive symptoms of schizophrenia. Moreover, PCP uniquely reproduced the type of cognitive dysfunction seen in schizophrenia. Mechanisms underlying PCP-induced psychosis remained largely unknown until the initial description of brain PCP receptors in 1979. Subsequent research in the early 1980s demonstrated that the PCP receptor constitutes a binding site located within the ion channel associated with N-methyl-D-aspartate (NMDA)-type glutamate receptors, and that PCP and related agents induce their psychotogenic effects by blocking NMDA receptor-mediated neurotransmission. This finding led to the suggestion (Reference 14; Reference 5) that endogenous dysfunction or dysregulation of NMDA receptor-mediated neurotransmission might contribute significantly to the etiology of schizophrenia, and, in particular, might lead to the expression of neuroleptic-resistant negative and cognitive symptoms. Further, it raised the possibility that medications that could potentiate NMDA receptor-mediated neurotransmission might be beneficial in the treatment of neuroleptic-resistant signs and symptoms of schizophrenia.

Prior to discovery of the glycine binding site in 1987, it was found that administration of oral glycine to rodents at high doses similar to those used later by the present inventor leads to reversal of behavioral effects induced by PCP (Reference 13), indicating that that behavioral assay may be sensitive to the anti-psychotic effects of NMDA augmenting agents.

NMDA receptors are primarily activated by glutamate, which serves as the major excitatory neurotransmitter in cortex. Exogenous glutamate cannot be administered effectively, however, because (1) glutamate does not cross the blood-brain barrier, (2) glutamate activates several types of receptors other than NMDA receptors, and (3) activation by glutamate analogs that cross the blood-brain barrier may lead to overexcitation of cortical neurons, resulting in neuronal degeneration (excitotoxicity). A potential alternate approach for potentiating NMDA receptor-mediated neurotransmission became available in 1987 with the demonstration that glycine acts as an allosteric modulator at the NMDA receptor complex (Reference 7). This finding raised the possibility that exogenously administered glycine might selectively potentiate NMDA receptor-mediated potentiation and might, therefore, lead to clinical improvement in schizophrenic patients with prominent neuroleptic-resistant symptomatology. Limitations to the use of glycine were (1) it was unknown to what extent exogenously administered glycine might permeate the CNS, (2) it was unknown to what extent glycine regulation of NMDA receptor-mediated neurotransmission would be of physiological relevance in vivo, and (3) it was unknown to what extent augmentation of NMDA receptor-mediated neurotransmission might, in fact, lead to clinical improvement.

Subsequent to the discovery of the glycine binding site in 1987, several small clinical trials were attempted which were suggestive of possible beneficial clinical effects but which failed to demonstrate efficacy using standard statistical approaches. Waziri in 1988 (Reference 12) published regarding the treating of 11 schizophrenic patients with doses of 5–25 g/day in an open study which lasted 9 months. They reported improvement in 4 of the 11 patients, but failed to provide a control group or statistical analysis of their results. Costa et al., in 1990 (Reference 2) published their work on treating 6 patients with doses of 15 g/day of glycine in a 5 week open design, and observed positive responses in 2 patients, as reflected in a greater than 30% decrease in symptoms as measured by the Brief Psychiatric Rating Scale (BPRS). However, overall statistical analysis was not performed, and independent analysis of their published data does not reveal a statistically significant effect (t=1.89, p=0.12). A subsequent study (Reference 19) of 18 patients in a double-blind study of 15 g/day of glycine vs. placebo showed significant improvement in Clinical Global Impression (CGI), but did not show significant improvement in either the BPRS or a scale developed specifically for the assessment of negative symptoms, the Schedule for Negative Symptoms (SANS). Although it was concluded by these authors that use of higher doses of glycine might be required to demonstrate efficacy, no follow-up studies were conducted. Rosse et al., (Reference 11, 1989) administered 10.8 g/day glycine to 6 chronic schizophrenic subjects for periods of 4 days to 8 weeks in an open-design but failed to observe overall clinical efficacy. These authors also concluded that this treatment approach was limited by the poor CNS permeation of glycine. Until 1994, no clinical studies were performed by any group with doses greater than 25 g/day, and the practicality of using glycine at higher doses was not determined.

The first study to be performed with higher doses of glycine was initiated in 8/89 and involved the work of the present inventor. In this study, 14 chronic schizophrenic subjects with neuroleptic-resistant symptomatology were treated with 0.4 g/Kg/day (approx. 30 g/day) in a double-blind placebo-controlled fashion and positive and negative symptoms were monitored using the Positive and Negative Symptom Scale (PANSS). This study validated the use of high doses of glycine in that the medication was well tolerated. Moreover, preliminary encouraging results were obtained such that significant improvement in negative symptoms was observed in the glycine-treated subjects, whereas no similar improvement was observed in those treated with placebo. However, the study remained inconclusive in that no significant difference was observed between the glycine- and placebo groups. Results of this study were published in August, 1994 (Javitt et al., 1994, Reference 6).

The present inventor and another disclose in their co-pending application a treatment with ultra-high (>30 g/day) doses of glycine for effective augmentation of NMDA receptor-mediated neurotransmission and for treatment of illness associated with psychosis and psychosis associated with drug intoxication, especially schizophrenia in vivo. Two recently completed studies validated this concept. In the first study (Leiderman et al., Reference 9), 5 schizophrenic subjects who had participated in the above-noted original 30 g/day glycine study at Bronx Psychiatric Center were rechallenged with a dose of 60 g/day. Glycine levels were monitored along with positive and negative symptoms, which were rated using both the SANS and PANSS. Treatment with 60 g/day of glycine was found to lead to a 6.3-fold increase in serum glycine levels. Such a rise in serum levels has been shown by others (D'Souza et al., 1995, Reference 3), to lead to an approximate doubling of CNS glycine levels. Thus, doses in excess of those used in prior studies (i.e., in excess of 30 g/day) may be required to significantly affect CNS glycine levels. No significant side effects were observed during treatment with 60 g/day of glycine. Thus, this study provided the first evidence of the practicality of clinical treatment with high-dose glycine. Finally, despite the small number of subjects significant improvement was observed on SANS negative symptoms (<0.05) and a trend toward significant improvement was observed on the PANSS, indicating potential efficacy of ultra-high dose glycine.

A second recently completed study provided more definitive evidence for the effectiveness of 60 g/day in the treatment of neuroleptic-resistant negative symptoms. This study was conducted by a former Bronx Psychiatric Center Schizophrenia Research Fellow, Dr. Uri Heresco-Levy, at the Sarah Herzog Hospital in Israel, in collaboration with the inventor and using the protocol developed by the inventor. Subjects were treated with 60 g/day of glycine vs. placebo in a double-blind crossover design. Results from the first 11 subjects were transmitted for analysis. These results demonstrate significantly greater reduction in PANSS negative symptoms in schizophrenic patients during the glycine-treatment phase than during the placebo-treatment phase. Thus, this study provides the first double blind, placebo-controlled evidence for efficacy of high-dose glycine treatment. Significant improvement was also observed in other aspects of schizophrenic symptomatology including general psychopathology and cognitive functioning. No significant side-effects were observed in any of the treated subjects.

Although the concept that treatment with oral glycine might be of significant clinical benefit in schizophrenia had been discussed in prior papers, the above-noted two recently completed studies (BPC and Israel) provided the first definitive evidence that a high dose glycine treatment is safe, practical and efficacious.

Up to 50% of schizophrenic subjects continue to show prominent negative and cognitive symptoms following treatment with neuroleptic medications. Newly developed agents, such as clozapine and risperidone, may show some improved efficacy compared to standard neuroleptics. Despite the introduction of such medications, however, significant numbers of schizophrenic patients remain chronically hospitalized. Treatment of such patients with glycine at doses of 30 g/day or above will lead to significant clinical improvement, and would thus address a clinical need that is not presently targeted by other available medications.

It was found treatment of psychotic conditions such as schizophrenic subjects with high (>30 g/day)-doses of oral glycine or agents which induce elevations in overall CNS glycine levels by serving as glycine precursors or which would substitute for glycine at the glycine site of the NMDA receptor complex (such as glycinamide, threonine and D-serine) lead to significant improvement in negative symptoms, depression and cognitive dysfunction without affecting positive symptoms or excitement. The glycine dose (0.8 g/Kg/day or approx. 60 g/day) that was used for the studies is substantially higher than the doses used in any prior study. Moreover, the serum glycine levels that resulted from the administration of 0.8 g/Kg/day of glycine are within the range of levels that are known to be associated with significant elevations of CNS glycine levels. The dosage range for the administration of glycine in accordance with the invention claimed in the above-identified co-pending patent application is above 0.4 g/Kg/day to about 2.0 g/Kg/day.

The precursor is administered in an amount sufficient for providing an equivalent elevation of extracellular glycine in the brain.

SUMMARY OF THE INVENTION

Limitations in the use of glycine and/or precursors are that (1) large doses must be administered, and (2) systems exist in the brain which serve to limit the degree to which exogenously administered glycine can increase glycine levels at critical sites within the brain.

This application describes an invention in which glycine uptake antagonists (also known as "glycine reuptake antagonists" and/or "glycine transport inhibitors") are used to augment NMDA receptor-mediated neurotransmission.

Glycine levels in brain are regulated via the action of glycine transporters (AKA uptake or reuptake pumps) which maintain low glycine levels in the vicinity of NMDA receptors (Reference 15; Reference 18). Blockade of glycine uptake, therefore, would increase glycine levels in the vicinity of NMDA receptors without, of necessity, increasing whole brain or net extracellular levels. Recent studies have been conducted with glycyldodecylamide (GDA), a compound which the applicant has recently shown to be an effective antagonist of glycine uptake in brain homogenate (Javitt and Frusciante, in press). These studies investigated the effects of GDA on PCP-induced hyperactivity in rodents, an assay system that has been shown to be sensitive to the effects of glycine (Reference 20) and other agents which potentiate NMDA receptor-mediated neurotransmission (Reference 19). Glycine (FIG. 5) and GDA (FIG. 6) showed similar profiles of activity in that both drugs inhibited PCP-induced hyperactivity without affecting baseline activity. GDA, however, was significantly more potent than glycine as evidenced by the fact that a dose of 0.05 g/kg GDA inhibited PCP-induced hyperactivity to the same degree as a dose of 0.8 g/kg glycine (equivalent to the dose of glycine used in clinical studies). Other GDA-like drugs also inhibited PCP-induced hyperactivity (FIG. 8) and their potency in blocking PCP-induced hyperactivity varied in proportion to their potency in inhibiting glycine uptake (FIG. 9). These findings indicate that glycine uptake antagonists will be as or more effective than glycine in treating PCP psychosis-like symptoms of schizophrenia (e.g., negative and cognitive symptoms). In this embodiment of the invention, human subjects would be treated with glycine uptake antagonists at doses which are effective in blocking glycine uptake in vitro and reversing PCP-induced hyperactivity in rodents in vivo. Two types of glycine uptake systems have been described in brain: GLYT1 transporters which are expressed in highest concentration in spinal cord, brainstem, diencephalon, and retina and to a lesser degree in olfactory bulb and cerebral hemispheres; and GLYT2 transporters which are restricted to spinal cord, brainstem and cerebellum (Reference 21). Moreover, GLYT1 transporters may exist in multiple isoforms which may arise, in part, through differential splicing (Reference 17). This embodiment of the invention would include inhibitors of either GLYT1- or GLYT2-mediated glycine uptake, including inhibitors of any isoform of said transporters.

In still another embodiment of the invention, psychosis associated with other psychiatric conditions including drug-induced (phencyclidine, ketamine and other dissociative anesthetics, amphetamine and other psychostimulants and cocaine) psychosis, psychosis associated with affective disorders, brief reactive psychosis, schizoaffective psychosis, and psychosis NOS, "schizophrenia-spectrum" disorders such as schizoid or schizotypal personality disorders, or illness associated with psychosis (such as major depression, manic depressive (bipolar) disorder, Alzheimers disease and post-traumatic stress syndrome) is treated.

In another embodiment of this application glycine uptake antagonists would be administered parenterally.

Other objects of the invention will be apparent to the skilled artisan from the detailed description of the invention herein.

DESCRIPTION OF THE DRAWING

FIGS. 2 (a)–(d) of the drawing depicts, from Study #2, three-factor and total PANSS change scores during double-blind adjunctive treatment with glycine and placebo (*p<0.05, p<0.01, *p<0.001).

FIGS. 3(a)–(d) of the drawing depicts, from Study #2, three-factor and total PANSS scores during double-blind adjunctive treatment with glycine and during the subsequent placebo period in 7 subjects who received glycine during the first treatment arm.

FIG. 13 of the drawing depicts, the relative inhibition of PCP- and amphetamine-induced hyperactivity by GDA (0.05 g/kg) in mice 0–90 minutes after PCP or amphetamine administration. Whereas GDA significantly antagonized PCP-induced hyperactivity (p=0.001, ***), it did not significantly affect amphetamine-induced hyperactivity. In the absence of PCP and amphetamine, integrated activity was <500 counts.

DETAILED DESCRIPTION OF THE INVENTION

Figure 1:
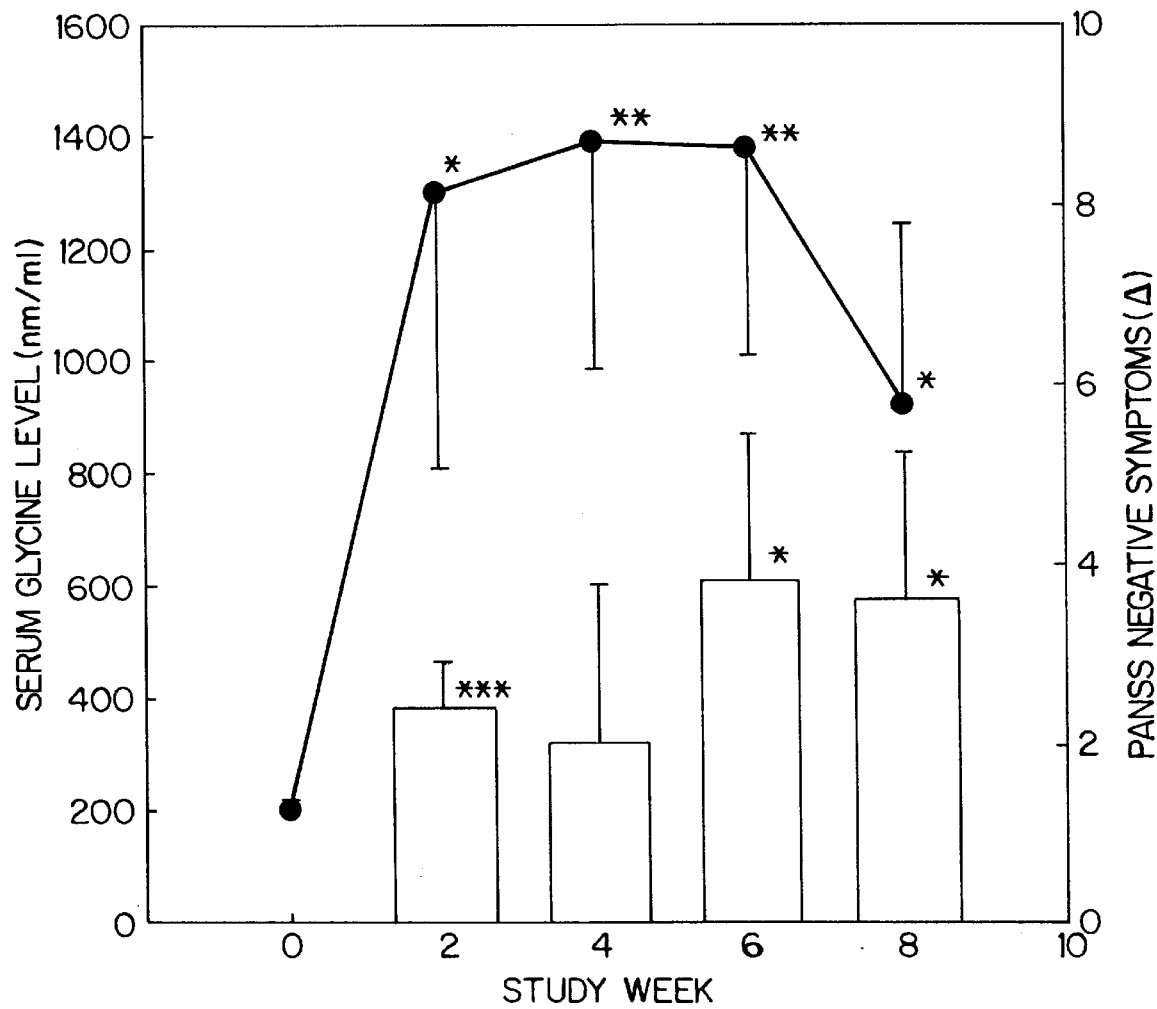
FIG. 1 of the drawing depicts effect of 0.8 g/Kg/day of oral glycine on serum glycine levels (scatter plot) and negative symptoms (bar plot) as determined using the Positive and Negative Symptom Scale (PANSS) (Kay et al., 1987, Reference 8) which includes such items as blunted affect, emotional or withdrawal, and difficulty in abstract thinking from Study #1. All statistics were performed using paired, two tailed t-tests (* p <0.1 vs. baseline (week 0),  p<0.05 vs. baseline, * p<0.01 vs. baseline).

Administration can be through the use of liquid and solid formulations and also through the use of injectables, such as intravenous injectables, wherein conventional pharmaceutical carriers would be employed. Suitable pharmaceutical preparations include tablets, capsules, oral liquids and parenteral injectables. Tablet and capsule formulations can be employed utilizing conventional diluents, excipients, and the like such as lactose in conventional capsule and tablet-making procedures. When administered as an oral liquid, some compounds may be made more palatable through the use of pleasant tasting diluents.

The compound for the present invention is to be administered at a dose sufficient to block total or partial glycine uptake. Glycine is effective above 0.4 g/Kg/day, for example, 0.5 g/Kg/day or above in one to several doses, preferably in a dose of 0.8 g/Kg/day divided into three equal doses in treating schizophrenia. The dose of the glycine uptake antagonist can be roughly determined by its inhibitory activity on PCP-induced hyperactivity compared with glycine. A convenient assay for evaluating augmentation of NMDA receptor-mediated transmission in vivo is the rodent assay used in study #3 hereinafter. At present, it is believed that GDA would be administered at a dose of about 0.025 g/Kg/day to 0.50 g/Kg/day, with doses of other compounds determined in relationship to GDA. The glycine uptake antagonist is given as the sole treatment for the psychotic-related condition, or is used adjunctively to conventional antipsychotic drugs such as haloperidol (Haldol®), fluphenazine (Prolixin®), chlorpromazine (Thorazine®) or thioridazine (Mellaril®), to atypical antipsychotic drugs such as clozapine (Clozaril®) and risperidone (Risperidal®), to medications used for the control of antipsychotic medication side effects, and to other medications commonly used for control of symptoms in conditions and illnesses such as schizophrenia.

When given in doses as herein, the glycine uptake antagonists would exert a clinically beneficial effect on symptoms of schizophrenia, in particular on negative symptoms and cognitive dysfunction. The beneficial effects of glycine uptake antagonists on negative symptoms occur in the absence of deterioration in any other aspects of schizophrenia, such as positive symptoms or excitement. In one embodiment of the invention, glycine uptake antagonist administration would be continued indefinitely for control of symptoms that do not respond adequately to traditional classes of medication.

The present invention contemplates the employment of any biologically acceptable glycine uptake antagonist for treatment of the noted disorders and diseases. Certain of the glycine uptake inhibitors are glyclyalkylamides, such as glycyldodecylamide and others used in study #3, are glycine alkyl esters. Other glycine uptake antagonists are known such as sarcosine. Once the concept of this invention is understood, the skilled artisan can employ any pharmacologically acceptable glycine uptake antagonist.

The following examples are provided to illustrate the effectiveness of glycine and glycine uptake antagonists for the treatment of schizophrenia.

Study #1 (Leiderman et al., supra.)

Methods: This study was conducted at the Bronx Psychiatric Center in the Bronx, N.Y. Five DSM-IV schizophrenic patients chosen because of participation in a prior double-blind study with 0.4 g/Kg/day of glycine entered this study after providing informed consent. Their mean age was 45.0±7.6 years old and their mean chronicity of illness 24.2±5.9 years. All were considered markedly to severely ill (CGI>4). All patients were receiving antipsychotics (2 clozapine, 2 risperidone and 1 haloperidol), on which they had been maintained for at least 4 weeks prior to the trial.

Oral glycine was added to their neuroleptic regimen at a dose of 10 g/day (~0.14 g/Kg/day), and incremented to 0.2 g/Kg/day (~14 g/day) at day 3. Glycine dose was increased by 0.2 g/Kg/day every 2 days until a dose of 0.8 g/Kg/day was reached, and was then maintained for the remainder of the 8 weeks treatment period. Biweekly ratings were performed using the Positive and Negative Syndrome Scale (PANSS) (Kay et al., 1987, Reference 8) and the Scale for the Assessment of Negative Symptoms (SANS) (Andreasen, 1989, Reference 1).

The Extrapyramidal Rating Scale (ERS) and the Abnormal Involuntary Movement Scale (AIMS) were used to measure motoric side effects. All ratings were performed by a single individual who was blind to outcome of the prior glycine treatment study. Glycine and neuroleptic blood levels for haloperidol and clozapine were obtained every two weeks. Plasma glycine was determined by a liquid chromatographic procedure (Harihan et al., 1993, Reference 4) for plasma amino acids and optimized for glycine using O-methylserine as an internal standard.

Values in text represent mean±standard deviation. Treatment effects were determined using two-tailed, paired t-tests.

Results: Treatment with oral glycine led to a significant, 6.3-fold increase in glycine blood levels that remained stable from week 2 to week 6 (FIG. 1). There was an apparent decrease in glycine level between weeks 6 and 8, although the difference did not reach statistical significance. No adverse effects, including weakness, nausea or sedation were seen in any patient during the 8 weeks of the trial.

A significant improvement in negative symptoms was found using the SANS (baseline: 75.8±7.2 vs. end of study: 72.2±8.6, t=2.79, p=0.049) and a trend towards improvement, using the PANSS negative symptom scale (baseline: 31.0±2.3 vs. end of the study: 27.4±3.2, t=2.21, p=0.092). Two of the 5 subjects experienced a greater than 20% reduction in negative symptoms. Treatment response was not significantly correlated with glycine level either across subjects or across time within individual subjects.

Of the patients included in this study, those who showed the greatest treatment response to glycine were those who had shown the greatest response to prior double-blind treatment with 0.4 g/Kg/day of glycine (Javitt et al., 1994, supra.). There was thus a significant across-subject correlation between change in total PANSS score observed in the present study and that observed in the prior study (r=0.82, p=0.045). As in the prior study, there were no significant changes in PANSS positive symptoms (t=1.68, df=4, p=0.17) or general psychopathology (t=0.72, df=4, p=0.5) in the present study. There was a significant reduction in extrapyramidal (t=4.81, df=4, p=0.009), but not dyskinetic (t=0.91, df=4, p=0.4), symptoms during glycine treatment. However, there was no correlation between improvement in extrapyramidal symptoms and clinical response. Glycine treatment did not significantly affect serum neuroleptic levels.

Study #2—Heresco-Levy, et al., above

Methods: Subjects consisted of inpatients drawn from the research unit of the Sarah Herzog Memorial Hospital, Jerusalem, Israel. Subjects were diagnosed with schizophrenia according to DSM-III-R (American Psychiatric Association, 1987). Subjects, moreover, were considered to be treatment resistant on the basis of poor response to prior neuroleptics. Prior to study entry, subjects had been treated with stable, clinically determined optimal oral doses of conventional neuroleptics or clozapine for at least 3 months. Schizophrenic patients who met the criteria of additional DSM-III-R diagnoses, were receiving additional psychotropic medications or had a concurrent medical or neurological illness were excluded. Twelve patients were enrolled in the study. All subjects gave written informed consent to participate and the study was approved by the institutional review board.

After a 2 week (week -2 to week 0) baseline assessment period, subjects were randomly assigned to receive, under double-blind conditions, either glycine powder or placebo solution for six weeks (week 0–week 6). Medication was administered under double blind conditions. Glycine powder was administered dissolved in water. The placebo solution consisted of glucose. Each patient then underwent a 2 week adjunctive treatment washout period after which he/she crossed over to the alternate substance for another 6 weeks (week 8–week 14). Glycine administration was initiated at a dose of 4 g/day and was increased by 4 g/day until a fixed daily dose equivalent to 0.8 g/Kg body weight was reached. Daily glycine treatment was administered in three divided doses. The only other medications allowed during the study were trihexyphenidyl (2–5 mg/day) for treatment of extrapyramidal symptoms and chloral hydrate (250–750 mg/day on PRN basis) for treatment of insomnia or agitation. For patients needing antiparkinsonian medication, trihexyphenidyl dose was kept constant throughout the study.

Symptoms and extrapyramidal side effects were assessed starting from week -2, biweekly throughout the study, using the PANSS, the Simpson-Angus Scale for Extrapyramidal Symptoms (SAS) and the Abnormal Involuntary Movement Scale (AIMS). Patients requiring, at any point during the study, neuroleptic dose increases were withdrawn from the study and appropriate treatment was instituted. Withdrawal decisions were based on clinical evaluations and coincided with an increase of at least 30% on the PANSS score.

Physical complaints and status were monitored daily. Hematology, blood chemistry, liver and kidney function, laboratory measures were assessed biweekly. Blood samples for the assessment of glycine serum levels were obtained at baseline and at the end of study weeks 6 and 14. Blood drawings were performed before breakfast and first daily administration of medication. Serum glycine levels were determined on a Perkin Elmer-Pickering Amino Acid Analyzer using a lithium pH gradient and postcolumn derivation with ninhydrin. Quantification was carried out using a UV detector at 570 mn. Calculations were based on a nor-leucine internal standard. Statistical analyses (two-tailed) were performed using the SPSS/PC computer program.

Results: Of the 12 patients who entered the study, 11 completed. The one early termination occurred at week 4 of placebo treatment. Of the patients who completed, 7 had been randomized to receive glycine during the first phase of the study, while the remaining 4 had been randomized to receive placebo. All patients showed stable pretreatment baselines as evidenced by a lack of change in positive and negative symptoms during the two weeks prior to double-blind treatment (Table 1). Pretreatment baselines did not differ among those subjects who received glycine during the first double-blind treatment phase and those who received placebo.

In order to assess treatment response to glycine relative to placebo, rmANOVA were performed across all subjects with within-subject factors of treatment phase (glycine/placebo) and treatment week (0, 2, 4 or 6). Highly significant between-treatment differences were observed for negative symptoms and general psychopathology, as reflected in significant treatment by time interactive effects, with no corresponding worsening of positive symptoms (Table 2). However, when changes in general psychopathology and total PANSS score were covaried for changes in negative symptom score, no significant treatment or treatment by time effects were observed, indicating that the changes in general psychopathology might have been secondary to changes in negative symptoms. Significant effects of glycine on total PANSS score was also observed. As with the general psychopathology effects, changes in total PANSS score were not significant following covariation for changes in negative symptoms. In order to assess the possibility that treatment order affected overall results, rmANOVA of negative symptoms by treatment phase and week were covaried for treatment order. Significance of the treatment by time effect $F(3,8)=42.6$, $p<0.0001$), indicating that results were not significantly affected by treatment order.

Analysis of symptom change scores revealed that significant reductions in negative symptoms were apparent by week 2 of the glycine treatment phase and increased progressively until termination of glycine treatment after week 6 (FIG. 2). The mean percentage reduction in negative symptoms at 6 weeks was $36.2\pm7.3\%$ compared to preglycine treatment values $t=0.22$, $df=10$, $p<0.0001$). Reductions in general psychopathology were first apparent after 4 weeks of glycine treatment and increased progressively thereafter. Mean reduction in general psychopathology was $23.5\pm10.5\%$ ($t=7.41$, $df=10$, $p<0.0001$). A small reduction in positive symptoms was also observed in the glycine treatment group ($12.6\pm18.3\%$). Although this effect was significant when compared to preglycine treatment values ($t=2.29$, $df=10$, $p<0.05$), changes in positive symptoms at the end of 6 weeks of glycine treatment were not significantly greater than changes following 6 weeks of placebo (FIG. 2). 8 of the 11 subjects had PANSS negative symptoms decreases of 30% or more and PANSS total score decreases of 25% or more during treatment with glycine. No reductions in symptoms of any type were apparent during the placebo treatment phase, and a small but significant increase in general psychopathology was observed at week 4 of the placebo treatment period.

Because 7 of the 11 subjects received glycine during the initial double blind, it was possible to evaluate the degree to which symptom improvement was maintained throughout the subsequent placebo treatment period (FIG. 3). No change in positive symptoms occurred in these 7 subjects during any phase of the study, whereas negative symptoms improved significantly during the glycine treatment phase ($F(3,4)=45.7$, $p=0.001$) and remained stable thereafter, with no significant worsening occurring during the subsequent placebo phase ($F(3,4)=1.86$, $p=0.28$). Similarly general psychopathology improved significantly during the glycine treatment phase ($F(3,4)=19.2$, $p<0.01$) and remained stable thereafter ($F(3,4)=2.52$, $p=0.20$), indicating that the improvements observed during glycine treatment were maintained during the subsequent 8 weeks of the study period.

5-factor analysis of the PANSS

Figure 4E:
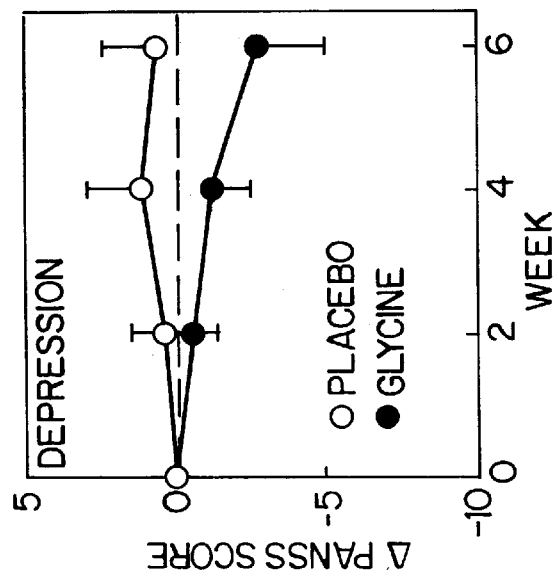
FIGS. 4 (a)–(e) of the drawing depicts, from Study #2, five-factor PANSS change scores during double-blind adjunctive treatment with glycine and placebo (*p <0.05, p <0.01, *p<0.001).
Figure 4D:
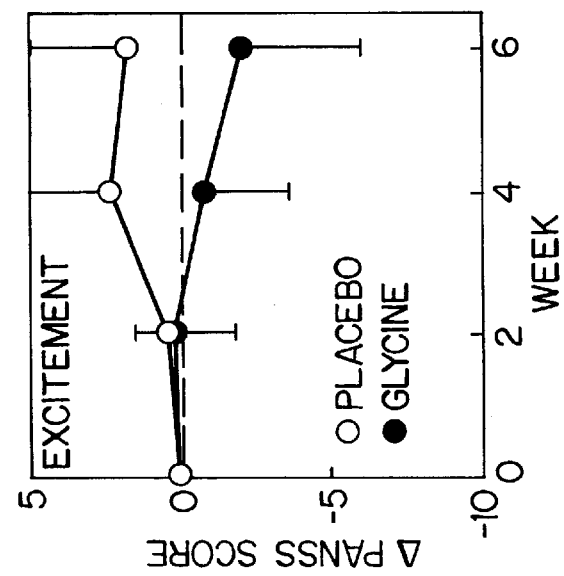
Figure 4C:
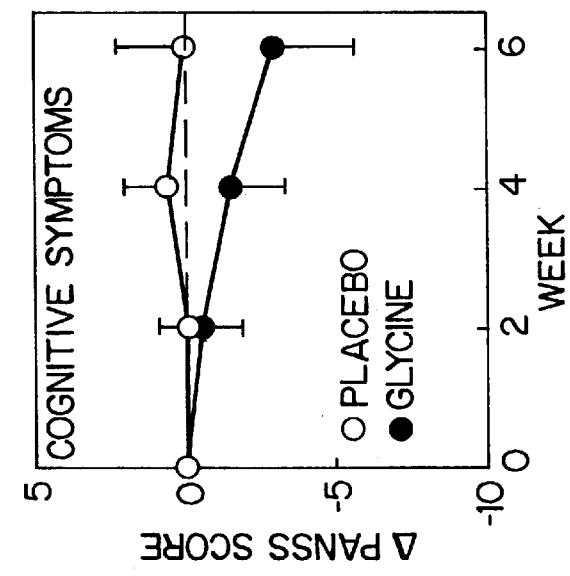
Figure 5:
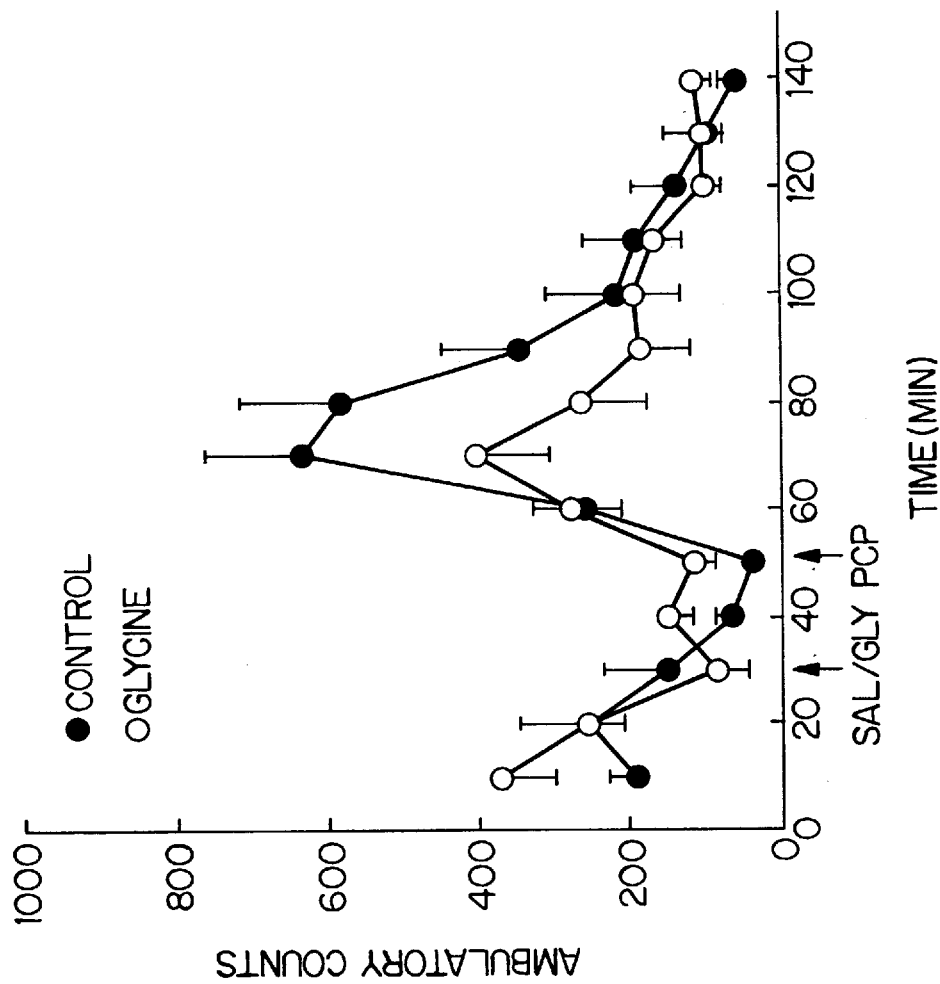
FIG. 5 of the drawing depicts, the effect of glycine on PCP-induced hyperactivity. Male BALB/c mice were pretreated with either glycine (0.8 g/kg) or placebo at time=30 min (first arrow). PCP (5 mg/kg sc.) was administered at time=50 min (second arrow) and ambulatory counts were monitored using an automated rodent activity chamber. Pretreatment with glycine led to an approximately 25% reduction in PCP-induced hyperactivity.
Figure 6:
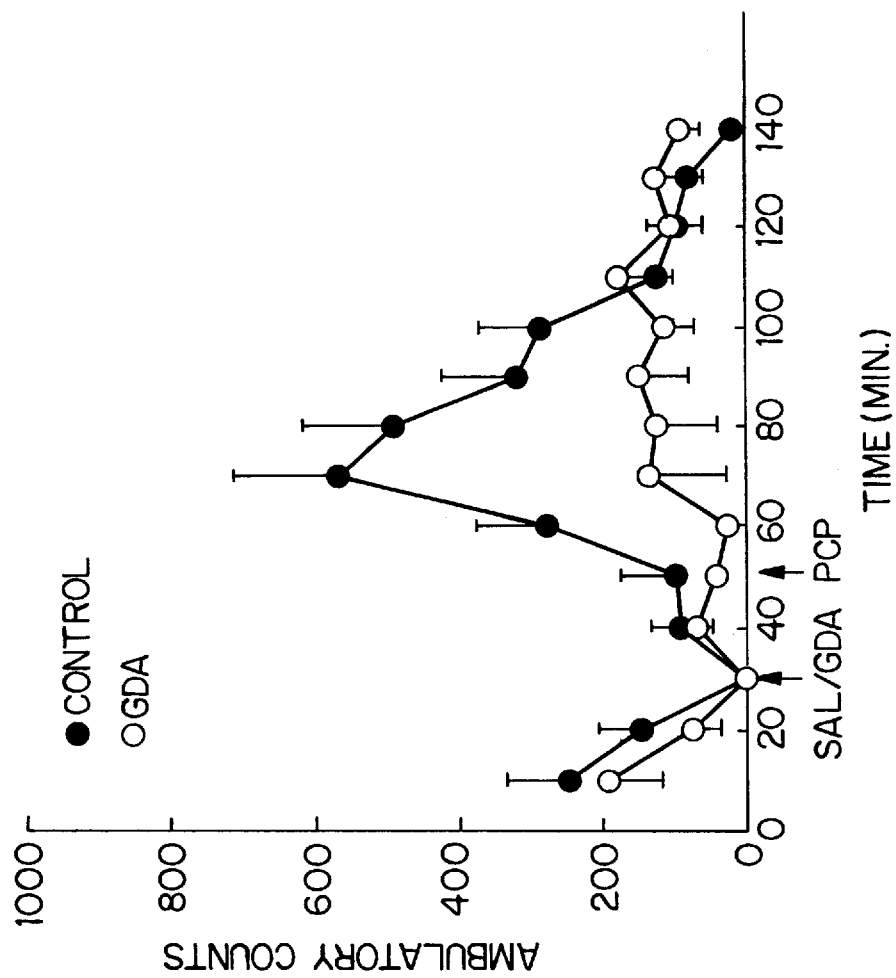
FIG. 6 of the drawing depicts, the effect of glycyldodecylamide (GDA) on PCP-induced hyperactivity. Male BALB/c mice were pretreated with either GDA (0.1 g/kg) or placebo at time=30 min (first arrow). PCP (5 mg/kg i.p.) was administered at time=50 min (second arrow) and ambulatory counts were monitored using an automated rodent activity chamber. Pretreatment with this dose of GDA led to an approximately 50% reduction in PCP-induced hyperactivity, with a similar pattern of effect observed previously for glycine.
Figure 7:
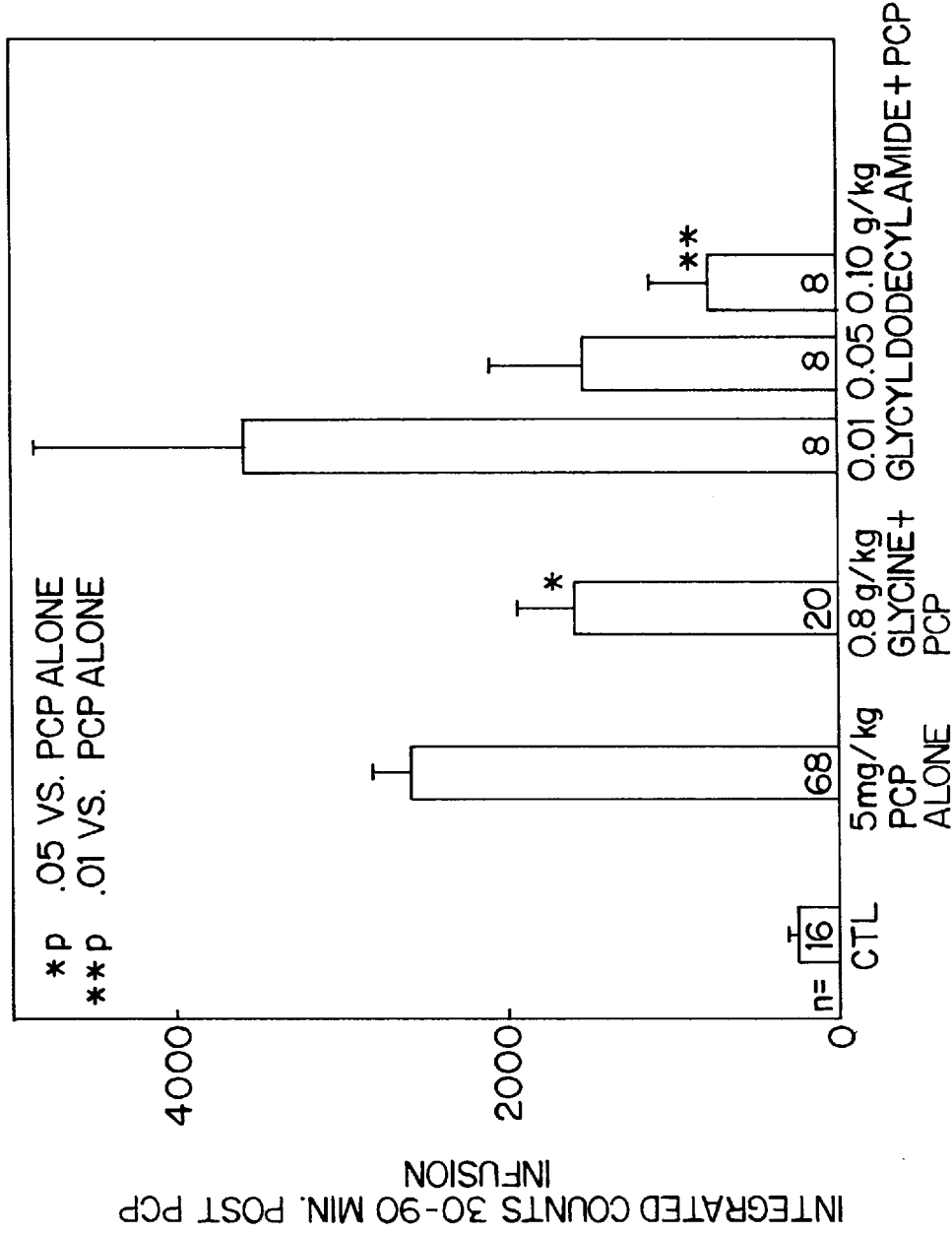
FIG. 7 of the drawing depicts, the effect of glycine and GDA on PCP-induced hyperactivity across the indicated number of experiments. A dose of 0.05 g/kg GDA led to a similar degree of behavioral inhibition as a dose of 0.8 g/kg glycine. A dose of 0.1 g/kg GDA was approximately twice as effective. *p<0.05 vs. PCP alone (CTL). ***p<0.001 vs. CTL FIG. 8 of the drawing depicts, the effect of several GDA-like compounds on PCP-induced hyperactivity, 0–90 minutes following 5 mg/kg, sc of PCP. The rank order of potency for these agents was glycyltriscadecylamide (GTA) >glycyldodecylamide (GDA)>glycylundecylamide (GUA).

Although traditional analysis of the PANSS divides symptoms into positive, negative and general clusters, alternative analyses have been proposed that incorporate either 5 or 7 factors. The 5 factor model divides symptoms into clusters that are labeled positive, negative, cognitive, depression and excitement. In order to determine the degree to which glycine affected dimensions of schizophrenia other than positive and negative, a secondary analysis of the data was performed using the 5-factor components (FIG. 4). As in the 3-factor analysis, no significant reduction in PANSS positive symptoms were observed during either glycine or placebo treatment, while significant, progressive improvement was observed during the glycine-, but not placebo-, treatment period (treatment by time $F(3,8)=19.5$, $p<0.0001$). Using the 5-factor analysis, however, significant reductions were also observed for depression ($F(3,8)=7.23$, $p<0.02$) and cognitive symptoms ($F(3,8)=4.74$, $p<0.05$). Improvements in depression ($F(3,5)=2.13$, $p=0.22$) and cognitive impairment ($F(3,5)=0.89$, $p=0.51$) did not remain significant following covariation for changes in negative symptoms. In contrast, the effect of glycine on negative symptoms remained significant even following covariation for changes in cognitive impairment or depression ($F(3,5)=6.8$, $p=0.032$). The percentage reduction was greatest for negative symptoms ($41.0\pm15.4\%$ decrease vs. preglycine levels, $p<0.0001$), followed by depression ($23.0\pm17.9\%$, $p=0.002$) and cognitive impairment ($15.2\pm13.5\%$, $p=0.004$). Reductions in excitement ($11.9\pm26.3\%$, $p=0.17$) and positive symptoms ($9.4\pm20.5\%$, $p=0.16$) did not reach statistical significance.

TABLE 1

3 Mean (sd) PANSS factor scores during prestudy baseline

| Factor | Week −2 | Week 0 |
|---|---|---|
| Positive symptoms | 23.1 (3.6) | 23.6 (3.2) |
| Negative symptoms | 35.6 (3.2) | 37.0 (6.5) |
| General psychopathology | 44.9 (13.2) | 45.5 (13.4) |
| Total PANSS score | 103.6 (20.6) | 105.5 (18.9) |

TABLE 2

3-factor PANSS scores during double-bind treatment with glycine (60 g/day)

| PANSS | Treatment | Treatment week | | | | Treatment | Time | Treat. × time |
|---|---|---|---|---|---|---|---|---|
| | | | PANSS Factor Scores - mean (sd) | | | | Statistical (rmANOVA) Results | |
| Positive | Glycine | 24.6 | 23.7 | 22.6 | 21.0 | F = 3.38 | F = 2.25 | F = 0.85 |
| | Placebo | 20.6 | 20.2 | 21.5 | 20.9 | | | |
| Negative | Glycine | 37.0 | 33.5 | 28.7 | 24.2 | F = 2.20 | F = 41.1 | F = 42.5 |
| | Placebo | 27.8 | 27.1 | 27.4 | 26.9 | | | |
| General | Glycine | 46.5 | 44.6 | 40.2 | 35.4 | F = 1.22 | F = 4.55 | F = 12.1 |
| | Placebo | 38.1 | 38.6 | 41.8 | 40.5 | | | |
| Total PANSS | Glycine | 108.1 | 101.8 | 91.7 | 80.6 | F = 2.93 | F = 16.6 | F = 13.4 |
| | Placebo | 86.6 | 85.9 | 90.6 | 88.3 | | | |

Study #3, Javitt and Frusciante, as above

Glycyldodecylamide (GDA) is a glycine derivative that was first described in 1986 (Reference 20). It was shown at that time to be significantly more potent than glycine in reversing PCP-induced hyperactivity. Further, it was shown that GDA administration did not lead to increased whole brain glycine levels, indicating that GDA did not act as glycine precursor. At the time, no mechanism for GDA-induced inhibition of PCP-induced hyperactivity was postulated.

Figure 10:
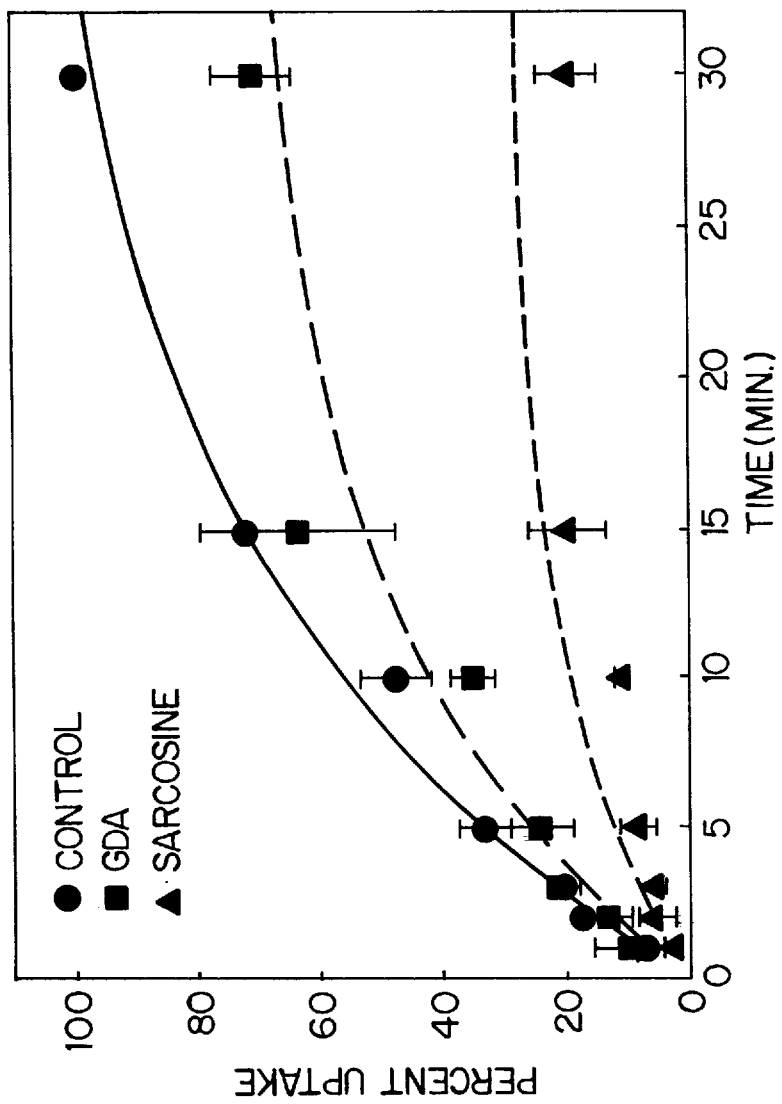
FIG. 10 of the drawing depicts, the kinetics of [$^3$H]glycine uptake into $P_2$ synaptosomes and inhibition by GDA and the known glycine uptake antagonist sarcosine. Points represent means±s.e.m. of three separate experiments, each performed in triplicate.

This study was undertaken to investigate the possibility that GDA reverses PCP-induced hyperactivity by blocking glycine reuptake in brain, thereby increasing glycine levels in the immediate vicinity of NMDA receptors. This hypothesis, while based upon the observation that GDA inhibits PCP-induced hyperactivity without increasing whole brain glycine levels, is not obvious from the prior literature. For glycine uptake studies, synaptosomal $P_2$ fractions were prepared from cortex of adult Sprague-Dawley rats and suspended in artificial CSF. Uptake of 100 nM [$^3$H]glycine was measured at 25° C. for the indicated time period in the presence of indicated ligands. Incubation was terminated by filtration under reduced pressure. Uptake was linear for at least the first 10 min of incubation (FIG. 10). Apparent plateau was reached at 30 min, with no significant increase in binding between 30 and 60 min. Kinetic binding parameters were determined by nonlinear regression. All uptake curves were determined to be first order. The mean $t_{1/2}$ value was $9.7\pm0.7$ min. The $IC_{50}$ value for inhibition of [$^3$H]glycine uptake by cold glycine was $78.7\pm37.8$ μM. Specific [$^3$H]glycine uptake was abolished in the absence of added $Na^+/Cl^-$.

Figure 11:
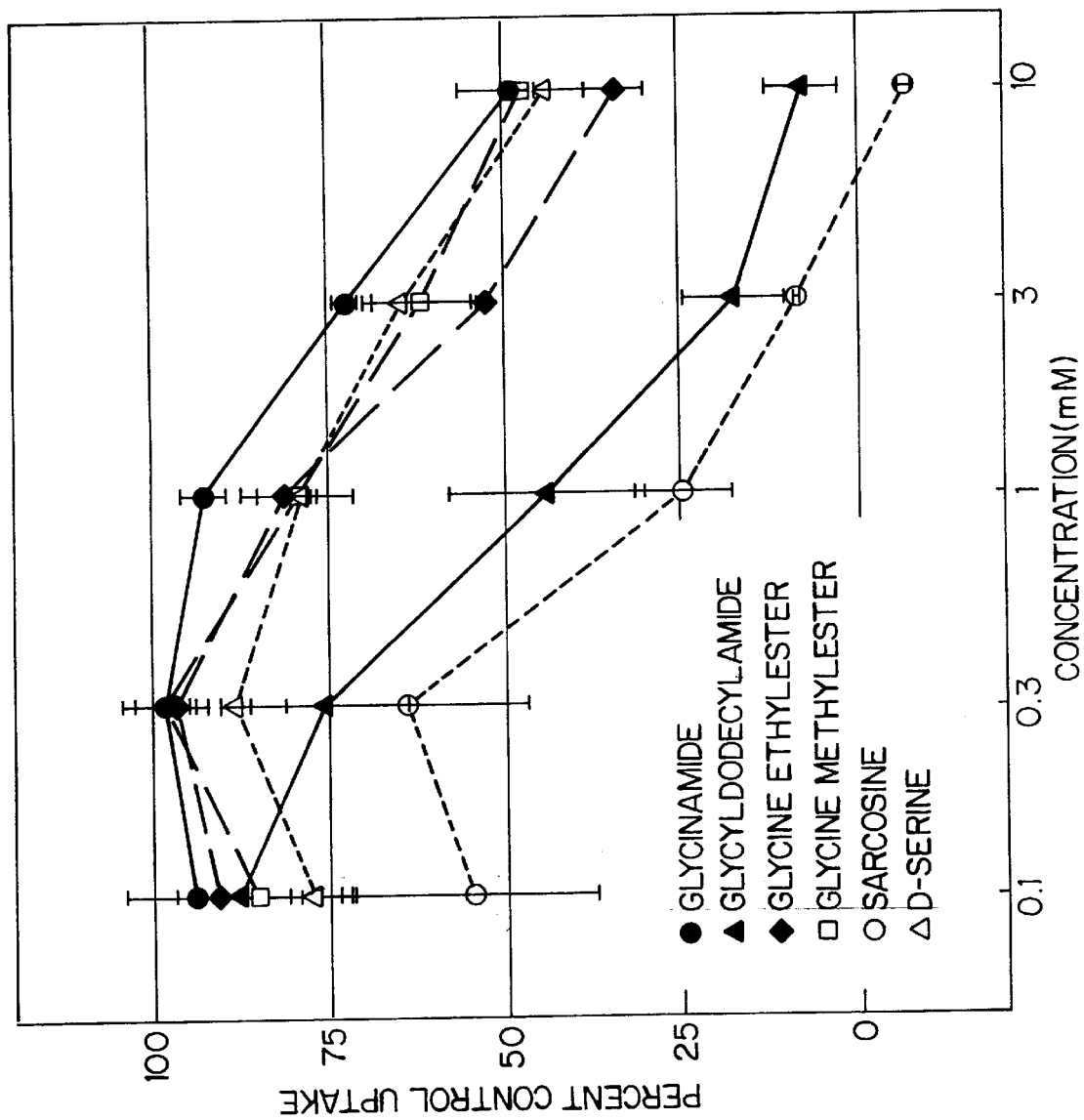
FIG. 11 of the drawing depicts, the inhibition of [$^3$H] glycine uptake by indicated glycine derivatives. Points represent means±s.e.m. of three separate experiments, each performed in triplicate.

Inhibition studies were conducted following 5 min incubation in the absence and presence of GDA concentrations between 0.1 and 10 mM (FIG. 11). Several comparison agents were also tested including (1) sarcosine, a known high potency glycine uptake antagonist, and (2) glycine ethyl ester (GEE) and glycine methyl ester (GME), agents with known lower affinity for the cortical glycine uptake site (Reference 18). The rank order of potency for inhibition of glycine uptake was glycine>sarcosine>GDA>GEE>GME. Both glycinamide and D-serine, which function as glycine precursors, showed $IC_{50}$ values of >10 mM. Effects of GDA and sarcosine remained significant throughout the 30 min incubation period. 1 mM concentrations of GDA and sarcosine significantly ($p<0.05$) reduced the maximal level of [$^3$H]glycine uptake by $29\pm7$ and $72\pm3\%$, respectively (FIG. 11). 5 mM GDA decreased maximal [$^3$H]glycine uptake by $51\pm13.3$. Effects of these agents on the rate constant of glycine uptake were not significant, although $t_{1/2}$ values in the presence of both GDA ($7.9\pm2.9$ $min^{-1}$) and sarcosine ($6.3\pm1.9$ $min^{-1}$) were somewhat lower than under baseline conditions. Given that the effective concentration of GDA in behavioral studies is approximately 0.3 mmol/kg, these studies demonstrate that GDA acts as a glycine uptake antagonist at a concentration similar to what may be obtained in behavioral studies.

Potential direct agonist-like effects of GDA at the glycine site of the NMDA receptor complex were excluded using PCP receptor binding as a functional probe of NMDA receptor activation. In this assay, glycine-like agents stimulate [$^3$H]MK-801 (available from Merck) binding in the presence, but not absence, of NMDA agonist (GLU, which is an abbreviation for glutamate). Assays were performed using crude synaptic membranes prepared from rat cortex and hippocampus and incubated for 15 min in 5 mM TRIS-acetate buffer (pH 7.4) in the presence of 1 nM

[³H]MK-801 and indicated ligands. Incubation was terminated by filtration under reduced pressure through Whatman GF/B filters. Nonspecific binding was determined in the presence of 10 µM MK-801. Incubation with GLU alone led to a 9-fold increase in binding compared to control conditions (Javitt and Frusciante, in press). Incubation with GLU and glycine led to a highly significant 22-fold increase compared to control conditions and a significant 2.5-fold increase compared to GLU alone. Binding in the presence of combined GLU and GDA was comparable to binding in the presence of GLU alone.

Specificity of glycine uptake antagonism by GDA was examined by evaluating the effects of glycine, GCA and GDA on uptake of GABA (gamma-aminobutyric acid) and GLU. Methods were the same as in the glycine uptake assay except that 10 nM concentrations of [³H]GABA or L-[³H] GLU were substituted for [³H]glycine. L-trans-pyrollidine-2,4-dicarboxyllic acid (L-PDC) and nipecotic acid were used as active controls for the GLU and GABA uptake assays, respectively. As opposed to its effects on [³H]glycine uptake, GDA significantly increased uptake of [³H]GLU and [³H]GABA. Given that activation of the glycine transporter in brain leads presynaptic GLU and GABA release, potentiation of GLU and GABA uptake is an expected in vitro consequence of glycine reuptake inhibition (Javitt and Frusciante, in press).

Figure 8:
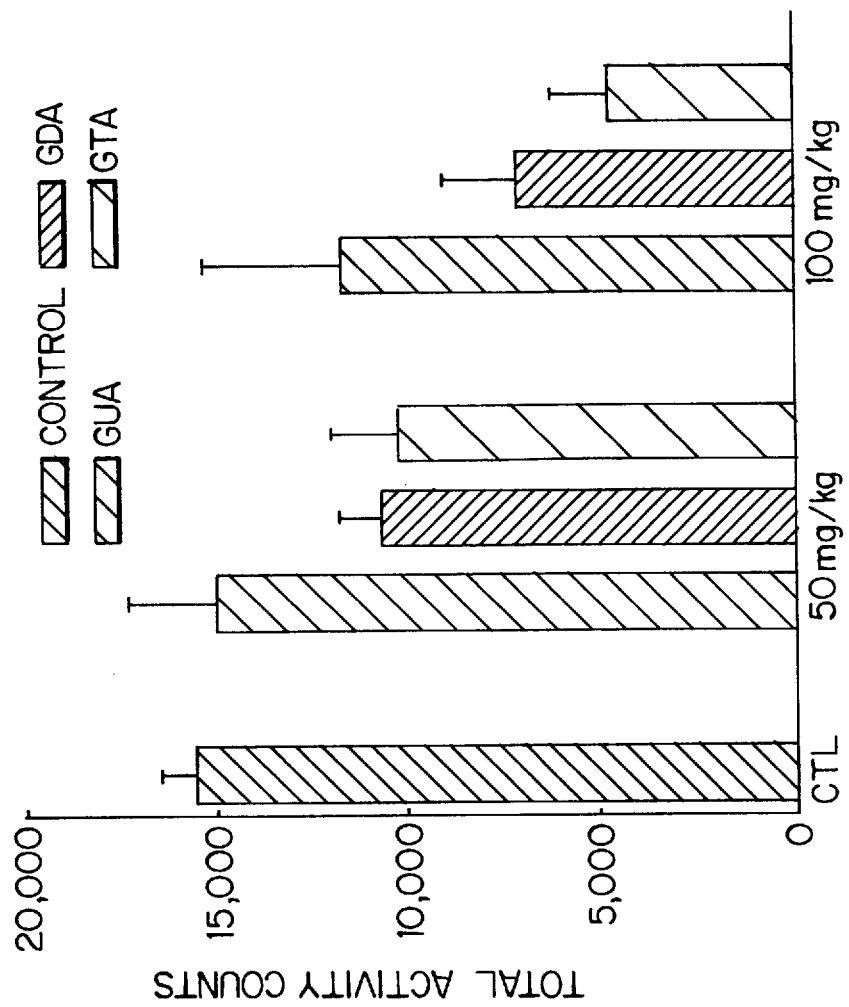
Figure 9:
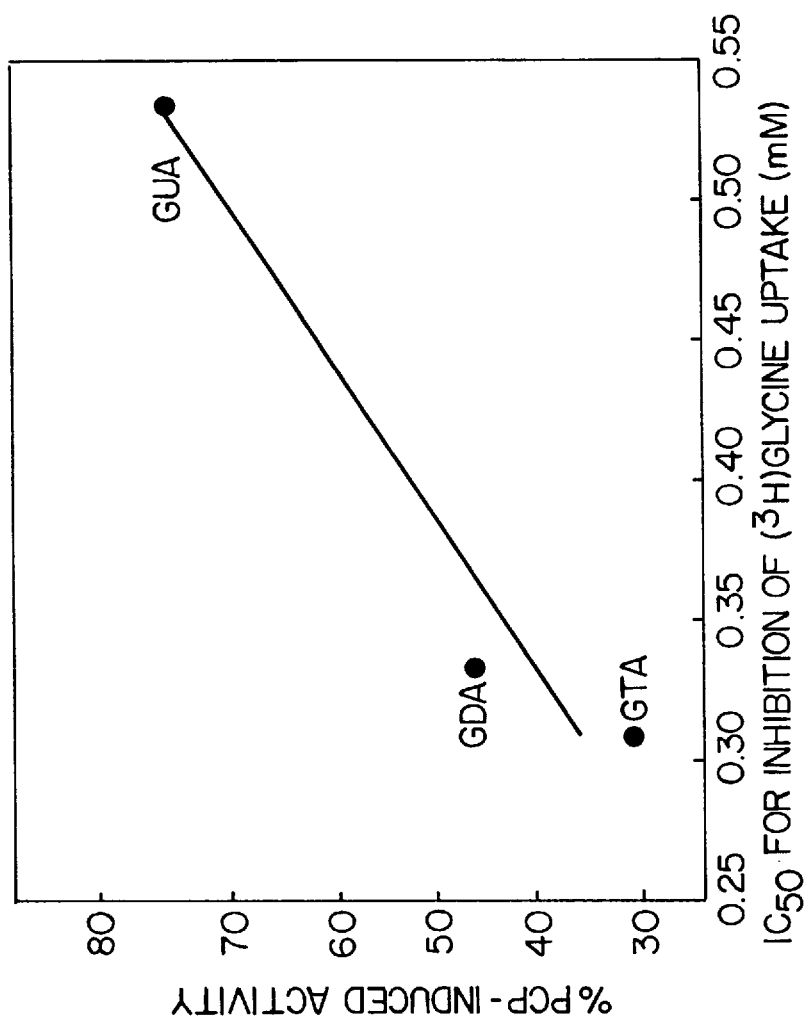
FIG. 9 of the drawing depicts, the relationship between potency for inhibition of PCP-induced hyperactivity (at 100 mg/Kg) in rodents and potency for inhibition of [$^3$H]glycine uptake in brain homogenate. The rank order of potency for inhibiting PCP-induced hyperactivity (% of PCP alone level) was the same as the rank order of potency for inhibiting [$^3$H]glycine uptake.
Figure 12:
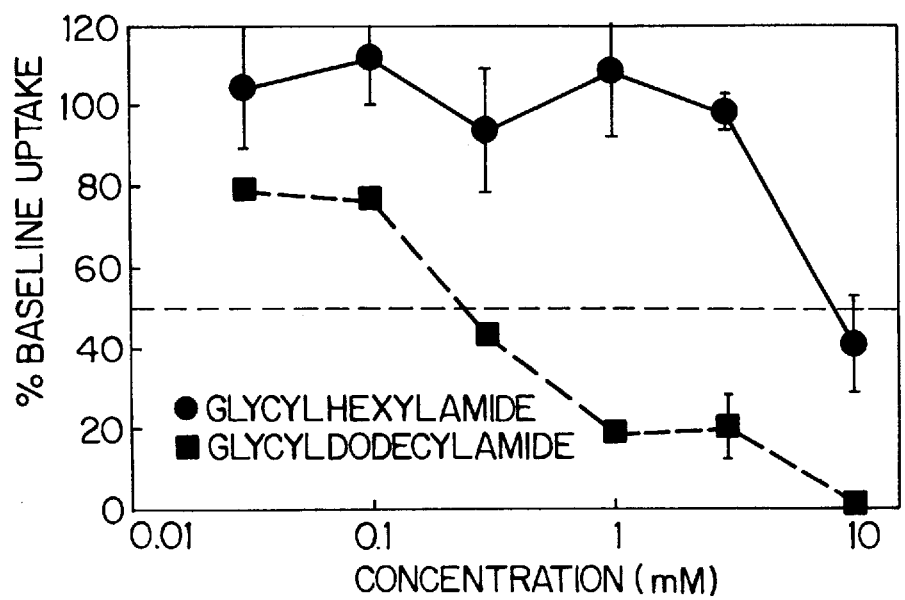
FIG. 12 of the drawing depicts, the inhibition of [$^3$H] glycine uptake by glycylhexylamide (GHA) relative to GDA. GHA, which is known to be ineffective in antagonizing PCP-induced hyperactivity at doses of up to 150 mg/kg, also shows very low potency for inhibition of [$^3$H]glycine uptake.

A subsequent study has investigated the rank order of potency of several GDA-like compounds for (1) inhibiting glycine uptake and (2) antagonizing PCP-induced hyperactivity in rodents. For this study, several additional compounds were synthesized, including glycyltriscadecylamide (GTA), glycylundecylamide (GUA), and glycylhexylamide (GHA). These compounds are glycinamide derivates which contain 13, 11 and 6 carbon atoms linked to the amide, respectively, as opposed to GDA which contains 12 carbons. GTA was found to be more potent that GDA both in inhibiting PCP-induced hyperactivity and in inhibiting glycine uptake (FIGS. 8,9). GUA was less effective in both assays. GHA, which was most recently synthesized, was found to be approximately 20-fold less potent that GDA in inhibiting glycine uptake (FIG. 12). This compound has previously been shown to be ineffective in blocking PCP-induced hyperactivity at doses of up to 0.15 g/kg (Reference 20).

In a recent experiment also, the effect of GDA on amphetamine-induced hyperactivity was evaluate as a control condition. Currently available antipsychotic agents, which exert their clinical effects primarily by blocking dopamine receptors, may reverse PCP-induced hyperactivity in rodents. However, they are less effective in blocking PCP-induced hyperactivity than hyperactivity induced by amphetamine (Reference 16). This study thus evaluated the effects of GDA on amphetamine-induced hyperactivity. A dose of GDA (0.05 g/kg) that potently and significantly (t=3.30, p=0.001) inhibited PCP-induced hyperactivity, did not significantly inhibit hyperactivity induced by amphetamine (t=0.59, NS) (FIG. 13).

Glycine has previously been shown not to inhibit amphetamine-induced hyperactivity (data not shown). These findings thus support the concept that GDA inhibits PCP-induced hyperactivity via a mechanism different from that of currently available antipsychotic agents.

In summary, this example demonstrates that GDA inhibits glycine uptake, and that a dose of 0.05 g/kg GDA induces a similar degree of inhibition of PCP-induced hyperactivity as a dose of 0.8 g/kg glycine, even though this dose of GDA is known not to lead to increases in whole brain glycine levels (although it may increase glycine levels in select brain compartments). At doses which are effective in blocking glycine uptake, GDA does not bind to NMDA receptors, or inhibit uptake of other amino acid neurotransmitters. GDA-like compounds inhibit PCP-induced hyperactivity in proportion to their potency in blocking cortical glycine uptake, and a GDA-like compound that is known to be relatively ineffective in blocking PCP-induced hyperactivity (glycylhexylamide) is also relatively ineffective in blocking glycine uptake. GDA also does not block amphetamine-induced hyperactivity at a dose that is effective in blocking PCP-induced hyperactivity. These findings provide the first demonstration that agents which block glycine uptake lead to behaviorally significant augmentation of brain NMDA receptor-mediated neurotransmission. Given the recent clinical finding that glycine leads to significant amelioration in symptoms of schizophrenia when given at doses similar to those which inhibit PCP-induced hyperactivity in rodents, the present findings indicate that GDA and other compounds which inhibit brain glycine uptake will be effective in the treatment of schizophrenia and other psychotic disorders.

REFERENCES

1. Andreasen N (1989): The scale for the assessment of negative symptoms (SANS): conceptual and theoretical foundations. Br J Psychiatry 155 (suppl. 7):49–52

2. Costa J, Khaled E, Sramek J, Bunney W Jr, Potkin S G (1990): An open trial of glycine as an adjunct to neuroleptics in chronic treatment-refractory schizophrenics. J Clin Psychopharmacol 10:71–72.

3. D'Souza D C, Morrissey K, Abi-Saab D, Damon D, Gil R, Bennett A, Krystal J H (1995): Intravenous glycine and oral D-cycloserine effects on CSF amino acids, plasma hormones, and behavior in healthy humans: Implications for schizophrenia. Schiz Res 15:147, 1995.

4. Hariharan M, Naga S, VanNoord T (1993): Systematic approach to the development of plasma amino acid analyses by high-performance liquid chromatography with ultraviolet detection with precolumn derivatization using phenyl isothiocyanate. J Chromatogr 621:15–22.

5. Javitt D C and Zukin S R (1991): Recent advances in the phencyclidine model of schizophrenia. Am J Psychiatry 148:1301–1308.

6. Javitt D C, Zylberman I, Zukin S R, Heresco-Levy U, Lindenmayer J P (1994): Amelioration of negative symptoms in schizophrenia by glycine. Am J Psychiatry 151:1234–1236.

7. Johnson J W. Ascher P. Glycine potentiates the NMDA response in cultured mouse brain neurons. Nature. 325:529–31, 1987.

8. Kay S R, Fiszbein A, Opler L A (1987): The positive and negative syndrome scale (PANSS) for schizophrenia. Schiz Bull 13:261–276

9. Leiderman Eduardo, Zylberman Ilana, Zukin Stephen R., Cooper Thomas B, Javitt Daniel C. (1996): Preliminary Investigation of High-Dose Oral Glycine on Serum Levels and Negative Symptoms in Schizophrenia: An Open-Label Trial. Biol Psychiatry 39:213–215.

10. Potkin S G, Costa J, Roy S, Sramek J, Jin Y, Gulasekaram B (1992): Glycine in the treatment of schizophrenia—theory and preliminary results, in Novel Antipsychotic Drugs (pp. 179–188). Edited by Meltzer H Y. New York, Raven Press.

11. Rosse R B, Theut S K, Banay-Schwartz M, Leighton M, Scarcella E, Cohen C G, Deutsch S I (1989): Glycine adjuvant therapy to conventional neuroleptic treatment in schizophrenia: an open-label, pilot study. Clin Neuropharmacol 12:416–24.

12. Waziri R (1989): Glycine therapy of schizophrenia. Biol Psychiatry 1988, 23:210–211 [letter].

13. Toth Eugene, Weiss Benjamine, Banay-Schwartz Miriam, Lajtha Abel (1986): Effect of Glycine Derivatives on Behavioral Changes induced by 3-Mercaptopropionic Acid or Phencyclidine in Mice. 11:1–8.

14. Javitt, D. C. (1987): Negative Schizophrenia Symptomatology and the PCP Model of Schizophrenia, Hillside Journal of Clinical Psychiatry, 9, 12–35.

15. Guastella J, Brecha N, Weigmann C, Lester H A, Davidson N (1992) Cloning, expression, and localization of a rat brain high-affinity glycine transporter. Proc Natl Acad Sci USA 89:7189–7193.

16. Jackson D M, Johansson C, Lindgren L-M, Bengtsson A (1994) Dopamine receptor antagonists block amphetamine- and phencyclidine-induced motor stimulation in rats. Pharmacol Biochem Behav 48:465–471.

17. Liu Q-R, Lopez-Corcuera B, Mandiyan S, Nelson H, Nelson, N (1993) Cloning and expression of a spinal cord- and brain-specific glycine transporter with novel structural features. J Biol Chem 1993; 268:22802–22808.

18. Smith K E, Borden L A, Hartig P R, Branchek T, Weinshank R L (1992) Cloning and expression of a glycine transporter reveal colocalization with NMDA receptors. Neuron 8:927–935.

19. Tanii Y, Nishikawa T, Hashimoto A, Takahashi K (1994) Stereoselective antagonism by enantiomers of alanine and serine of phencyclidine-induced hyperactivity, stereotypy and ataxia in the rat. J Pharmacol Exp Ther 269:1040–1048.

20. Toth E, Lajtha A (1986) Antagonism of phencyclidine-induced hyperactivity by glycine in mice. Neurochem Res 11:393–400.

21. Zafra F, Aragon C, Olivares L, Danbolt N C, Gimenez C, Storm-Mathisen J (1995) Glycine transporters are differentially expresses among CNS cells. J Neurosci 15:3952–3969.

From the above, the effectiveness of this invention for treating symptoms of schizophrenia can be seen.

The skilled artisan will be able to select other naturally occurring and synthetic, i.e., of presently known and to be discovered chemical structures, glycine uptake antagonists for use in providing an antipsychotic effect.

Variations of the invention will be apparent to the skilled artisan.

What is claimed is:

1. A process for augmenting NMDA receptor-mediated neurotransmission in a human in need thereof which comprises administering to said human a glycine uptake antagonist in an amount sufficient for augmenting NMDA receptor-mediated neurotransmission.

2. A process for treating a psychosis in a human patient having a psychosis which comprises administering to said human a glycine uptake antagonist in an amount sufficient for augmenting NMDA receptor-mediated neurotransmission.

3. The process of claim 2 wherein the psychosis is associated with an illness.

4. The process of claim 2 wherein the illness is major depression, manic-depressive (bipolar) disorder, Alzheimers disease or post-traumatic stress syndrome.

5. The process of claim 2 wherein the psychosis is associated with drug intoxication.

6. The process of claim 5 wherein the drug is a dissociative anesthetic or a psychostimulant.

7. A process for treating schizophrenia in a human patient which comprises administering to said patient a glycine uptake antagonist in an amount sufficient for augmenting NMDA receptor-mediated neurotransmission.

8. The process of claim 7 in which an antipsychotic drug is also administered to the patient.

9. The process of claim 8 wherein the anti-psychotic drug is a neuroleptic drug.

10. The process of claim 1 wherein the glycine uptake antagonist inhibits GLYT1 or GLYT2-mediated glycine uptake.

11. The process of claim 2 wherein the glycine uptake antagonist inhibits GLYT1 or GLYT2-mediated glycine uptake.

12. The process of claim 7 wherein the glycine uptake antagonist inhibits GLYT1 or GLYT2-mediated glycine uptake.

* * * * *